US00PP22857P2

(12) United States Plant Patent
Hooijman

(10) Patent No.: US PP22,857 P2
(45) Date of Patent: Jul. 17, 2012

(54) ROSE PLANT NAMED 'ESM PACARINA'

(50) Latin Name: *Rosa hybrida*
Varietal Denomination: ESM Pacarina

(75) Inventor: Aloysius A. J. Hooijman, Aalsmeer (NL)

(73) Assignee: Esmeralda Breeding B.V., Aalsmeer (NL)

( * ) Notice: Subject to any disclaimer, the term of this patent is extended or adjusted under 35 U.S.C. 154(b) by 140 days.

(21) Appl. No.: 12/807,249

(22) Filed: Aug. 31, 2010

(51) Int. Cl.
*A01H 5/00* (2006.01)

(52) U.S. Cl. ..... Plt./130

(58) Field of Classification Search ..... Plt./130, Plt./135
See application file for complete search history.

*Primary Examiner* — Annette Para
(74) *Attorney, Agent, or Firm* — C. A. Whealy

(57) ABSTRACT

A new and distinct cultivar of Rose plant named 'Esm Pacarina', characterized by its long, moderately strong and upright flowering stems; durable foliage; yellow orange-colored flowers with orange and orange red-colored margins; good postproduction longevity; and resistance to Botrytis.

1 Drawing Sheet

Botanical designation: *Rosa hybrida.*
Cultivar denomination: 'ESM PACARINA'.

BACKGROUND OF THE INVENTION

The present Invention relates to a new and distinct cultivar of Rose plant, botanically known as *Rosa hybrida*, commercially used as a cut flower Rose plant, and hereinafter referred to by the name 'Esm Pacarina'.

The new Rose plant is a product of a planned breeding program conducted by the Inventor in El Quinche, Pichincha, Ecuador. The objective of the breeding program was to develop new freely-flowering cut flower Rose varieties with novel and attractive flower colors and excellent postproduction longevity.

The new Rose plant originated from a cross-pollination made by the Inventor in February, 2000 of a proprietary Rose selection identified as code name Line 53, not patented, as the female, or seed, parent with a proprietary Rose selection identified as code name Line 50, not patented, as the male, or pollen, parent. The new Rose plant was discovered and selected by the Inventor as a single flowering plant within the progeny of the stated cross-pollination in a controlled greenhouse environment in El Quinche, Pichincha, Ecuador in March, 2001.

Asexual reproduction of the new Rose plant by cuttings at El Quinche, Pichincha, Ecuador since April, 2001, has shown that the unique features of this new Rose plant are stable and reproduced true to type in successive generations of asexual reproduction.

SUMMARY OF THE INVENTION

Plants of the new Rose have not been observed under all possible environmental conditions. The phenotype may vary somewhat with variations in environment such as temperature and light intensity, without, however, any variance in genotype.

The following traits have been repeatedly observed and are determined to be the unique characteristics of 'Esm Pacarina'. These characteristics in combination distinguish 'Esm Pacarina' as a new and distinct Rose plant:

1. Long, moderately strong and upright flowering stems.
2. Durable foliage.

3. Yellow orange-colored flowers with orange and orange red-colored margins.
4. Good postproduction longevity.
5. Resistant to Botrytis.

Plants of the new Rose differ from plants of the female parent selection in the following characteristics:

1. Plants of the new Rose are smaller than plants of female parent selection.
2. Plants of the new Rose have smaller flowers than plants of the female parent selection.
3. Plants of the new Rose and the female parent selection differ in flower color as plants of the female parent selection have dark pink and red bi-colored flowers.

Plants of the new Rose differ from plants of the male parent selection in the following characteristics:

1. Plants of the new Rose are more freely flowering than plants of the male parent selection.
2. Plants of the new Rose have slightly smaller flowers than plants of the male parent selection.
3. Plants of the new Rose and the male parent selection differ in flower color as plants of the male parent selection have salmon pink-colored flowers.

Plants of the new Rose can be compared to plants of Rose 'Korlumara', not patented. In side-by-side comparisons conducted in El Quinche, Pichincha, Ecuador, plants of the new Rose differed from plants of 'Korlumara' in the following characteristics:

1. Plants of the new Rose were not as vigorous as plants of 'Korlumara'.
2. Plants of the new Rose had smaller leaves than plants of 'Korlumara'.
3. Plants of the new Rose had slightly smaller flowers than plants of 'Korlumara'.
4. Plants of the new Rose had fewer petals per flower than plants of 'Korlumara'.

BRIEF DESCRIPTION OF THE PHOTOGRAPH

The accompanying colored photograph illustrates the overall appearance of the new Rose plant showing the colors as true as it is reasonably possible to obtain in colored reproductions of this type. Colors in the photographs may differ slightly from the color values cited in the detailed botanical description which accurately describe the colors of the new Rose plant.

The photograph at the left of the sheet comprises a side perspective view of a typical flowering stem of 'Esm Pacarina'.

The photograph at the upper right of the sheet is a top perspective close-up view of a typical flower of 'Esm Pacarina'.

The photograph at the center of the sheet is a close-up view of the upper and lower surfaces of typical petals of 'Esm Pacarina'.

The photographs at the lower right of the sheet are close-up views of the upper and lower surfaces of typical leaves of 'Esm Pacarina'.

DETAILED BOTANICAL DESCRIPTION

Plants of the new Rose have not been observed under all possible environmental conditions. The phenotype may vary somewhat with variations in environment such as temperature and light intensity, without, however, any variance in genotype. The aforementioned photographs, following observations and measurements describe plants grown in ground beds in a polyethylene-covered greenhouse in El Quinche, Pichincha, Ecuador and under commercial Rose production practices. Plants were pinched about 13 to 14 weeks after planting. Plants were three years old when the photographs and description were taken. During the production of the plants, day temperatures ranged from 16° C. to 30° C., night temperatures ranged from 12° C. to 16° C. and light levels ranged from 800 to 1,200 foot-candles. In the following description, color references are made to The Royal Horticultural Society Colour Chart, 2001 Edition, except where general terms of ordinary dictionary significance are used.

Botanical classification: *Rosa hybrida* 'Esm Pacarina'.

Parentage:

*Female, or seed, parent*.—Proprietary seedling selection of *Rosa hybrida* identified as code name Line 53, not patented.

*Male, or pollen, parent*.—Proprietary seedling selection of *Rosa hybrida* identified as code name Line 50, not patented.

Propagation:

*Type*.—By cuttings.

*Time to initiate roots*.—About seven to ten days at 26° C. to 30° C.

*Time to produce a rooted young plant*.—About four to five weeks at 22° C. to 26° C.

*Root description*.—Fibrous, medium in thickness; close to N199B in color.

*Rooting habit*.—Freely branching; moderately dense.

Plant description:

*Plant form*.—Upright plant habit; long, moderately strong and upright flowering stems.

*Growth habit*.—Moderately vigorous; freely basal branching habit; dense and bushy growth habit; about 14.4 flowering stems develop per year.

*Plant height*.—About 68 cm.

*Plant width* (*spread*).—About 52 cm.

*Lateral branches* (*peduncles*).—Length: About 68 cm. Diameter: About 5.1 mm. Internode length: About 5.2 cm. Texture: Smooth, glabrous. Color: Close to 146A becoming closer to N199A with development. Thorns: Density: Medium to high. Shape: Triangular with sharp acuminate apices. Height: About 7.8 mm. Length, at base: About 9.3 mm. Color, immature: Close to 183A becoming closer to 160B with development. Color, mature: Close to 161B.

Foliage description:

*Arrangement*.—Alternate; compound with typically five leaflets per leaf.

*Leaf length*.—About 15.3 cm.

*Leaf width*.—About 9.2 cm.

*Terminal leaflet length*.—About 5.6 cm.

*Terminal leaflet width*.—About 4.3 cm.

*Lateral leaflet length*.—About 4.5 cm.

*Lateral leaflet width*.—About 3.6 cm.

*Leaflet shape*.—Oval.

*Leaflet apex*.—Acute.

*Leaflet base*.—Attenuate.

*Leaflet margin*.—Serrate.

*Leaflet texture, upper and lower surfaces*.—Smooth, glabrous.

*Leaflet venation pattern*.—Pinnate.

*Leaflet color*.—Developing leaflets, upper surface: Close to 147A. Developing leaflets, lower surface: Close to 147B tinged with close to 166A. Fully expanded leaflets, upper surface: Close to 147A and 139A; venation, close to N144A. Fully expanded leaflets, lower surface: Close to 147B; venation, close to 146C.

*Petioles, leaves*.—Length: About 1.7 cm. Diameter: About 1.5 mm. Texture, upper and lower surfaces: Pubescent. Color, upper surface: Close to 146A. Color, lower surface: Close to 144A.

*Petioles, leaflets*.—Length: About 2.3 cm. Diameter: About 1.1 mm. Texture, upper and lower surfaces: Pubescent. Color, upper surface: Close to 146A tinged with close to 187A. Color, lower surface: Close to 144A.

*Stipules*.—Quantity/arrangement/appearance: Two, adnate to the petiole, leafy. Length: About 2.8 cm. Width: About 3 mm. Shape: Roughly deltoid. Apex: Acuminate. Base: Truncate. Margin: Serrate, irregular. Texture, upper and lower surfaces: Pubescent. Venation pattern: Pinnate. Color, upper surface: Close to 137A. Color, lower surface: Close to 138A.

Flower description:

*Flower type and habit*.—Symmetrical rosette flowers; typically grown as a single stem.

*Flowering season*.—Year-round under greenhouse conditions, plants begin flowering about 65 to 67 days after planting; in the garden, optimal flowering from spring through autumn; flowering intermittent.

*Flower diameter*.—About 9 cm.

*Flower depth* (*height*).—About 4.8 cm.

*Flower longevity on plant*.—About 30 days; flowers persistent.

*Flower longevity as a cut flower*.—About 14 days.

*Fragrance*.—Slightly fragrant, pleasant.

*Flower buds*.—Shape: Cupped. Length: About 5 cm. Diameter: About 4.3 cm. Color: Close to 144A tinged with close to 165A.

*Petals*.—Quantity: About 30 per flower; petals imbricate. Length: About 5.2 cm. Width: About 5.3 cm. Shape: Nearly round; transversely ovate. Apex: Blunt to acute. Base: Obtuse. Margin: Entire. Texture, upper and lower surfaces: Smooth, glabrous. Color: When opening, upper surface: Center, close to N30A diffusing to N25C; towards the base, close to 14A; towards the margins, close to 46A. When opening, lower surface: Center, close to 12A; towards the margins, close to N30C and N25C; towards the apical margin, close to 46A. Fully opened, upper surface: Center, close to 9A; towards the margins, close to N34C to N34A; margins of outer petals, close to 45D. Fully opened, lower surface: Center, close to 12B; towards the margins, close to 45C; outer petals with random tinging of close to 45D.

*Sepals*.—Quantity per flower: Typically five. Length: About 4.6 cm. Width: About 1.3 cm. Shape: Roughly deltoid. Apex: Tapered. Base: Truncate. Margin: Entire; ciliate. Texture, upper and lower surfaces: Pubescent; leathery. Color: When opening, upper surface: Close to 144C tinged with close to 46B. When opening, lower surface: Close to 144A. Fully opened, upper surface: Close to 143A and 144C. Fully opened, lower surface: Close to 144A to 144C.

*Reproductive organs*.—Stamens: Quantity: About 117 per flower. Anther length: About 3 mm. Anther shape: Reniform. Anther color: Close to 162A; towards the margins, close to N163D. Filament color: Close to 13A. Pollen amount: Abundant. Pollen color: Close to N163C. Pistils: Quantity: About 118 per flower. Pistil length: About 1.5 cm. Stigma shape: Broadly reniform. Stigma color: Close to 163B. Style length: About 9.8 mm. Style color: Close to 145C tinged with close to 41A. Receptacle height: About 1.5 cm. Receptacle diameter: About 1.1 cm. Receptacle shape: Cup-shaped. Receptacle texture: Smooth, glabrous. Receptacle color: Close to 144A. Fruits: Length: About 2.5 cm. Diameter: About 1.7 cm. Texture: Smooth. Color: Close to 146D becoming closer to 167D with development. Seeds: Quantity per fruit: About ten. Length: About 7 mm. Diameter: About 5 mm. Texture: Smooth. Color: Close to 153D.

Pathogen/pest resistance: Plants of the new Rose have been observed to be resistant to Botrytis. Plants of the new Rose have not been observed to be resistant to pests and other pathogens common to Roses.

Temperature tolerance: Plants of the new Rose have been observed to tolerate temperatures ranging from 0° C. to 35° C.

It is claimed:

1. A new and distinct Rose plant named 'Esm Pacarina' as illustrated and described.

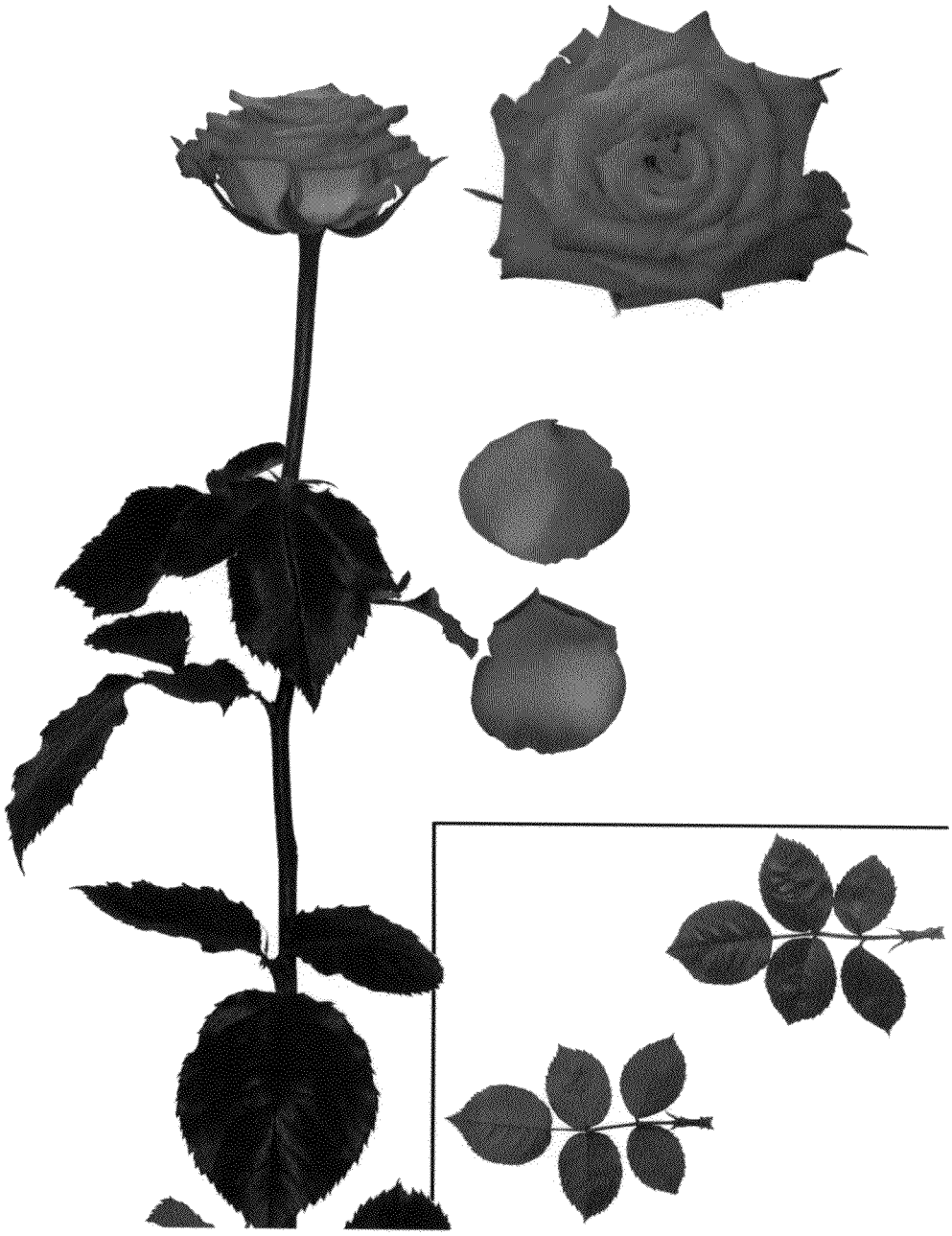

* * * * *